United States Patent
Hall et al.

(10) Patent No.: US 8,201,966 B2
(45) Date of Patent: Jun. 19, 2012

(54) ILLUMINATION DEVICE

(75) Inventors: Graeme Hall, Leeds (GB); Euan Morrison, Cambridge (GB)

(73) Assignee: Brandon Medical Company Limited, Leeds (GB)

( * ) Notice: Subject to any disclaimer, the term of this patent is extended or adjusted under 35 U.S.C. 154(b) by 451 days.

(21) Appl. No.: 12/523,426

(22) PCT Filed: Jan. 16, 2008

(86) PCT No.: PCT/GB2008/000142
§ 371 (c)(1),
(2), (4) Date: Jul. 16, 2009

(87) PCT Pub. No.: WO2008/087404
PCT Pub. Date: Jul. 24, 2008

(65) Prior Publication Data
US 2010/0002428 A1    Jan. 7, 2010

(30) Foreign Application Priority Data

Jan. 18, 2007  (GB) .................................. 0700935.0
May 17, 2007  (GB) .................................. 0709508.6

(51) Int. Cl.
  *F21V 9/00*  (2006.01)
(52) U.S. Cl. .................. 362/231; 362/293; 362/249.02; 362/240
(58) Field of Classification Search .................. 362/230, 362/231, 293, 84, 249.02, 249.06, 240–245
See application file for complete search history.

(56) References Cited

U.S. PATENT DOCUMENTS

| | | |
|---|---|---|
| 2004/0264193 A1 | 12/2004 | Okumura |
| 2005/0117125 A1 | 6/2005 | Minano et al. |
| 2005/0195599 A1 | 9/2005 | Marka |
| 2005/0286264 A1* | 12/2005 | Kim et al. .................... 362/600 |
| 2006/0285323 A1 | 12/2006 | Fowler |
| 2008/0212319 A1* | 9/2008 | Klipstein .................... 362/231 |

FOREIGN PATENT DOCUMENTS

| | | |
|---|---|---|
| DE | 102005043783 A1 | 10/2006 |
| EP | 1462711 A | 9/2004 |
| EP | 1568935 A | 8/2005 |
| EP | 1647763 A | 4/2006 |
| EP | 1741975 A | 1/2007 |
| WO | WO-0136864 A2 | 5/2001 |
| WO | WO-0206723 A1 | 1/2002 |

OTHER PUBLICATIONS

Chenhua You: "Visual equivalence of light emitting diode white light" Optical Engineering, vol. 44, No. 11, Nov. 1, 2005, pp. 111307-1-111307-7, XP007904563 (Abstract Only).

Y. Ohno: "Simulation Analysis of White LED Spectra and Color Rendering" PROC, CIE Symposium '04, LED Light Sources: Physical Measurement and Visual and Photobiological Assessment, [Online] XP002477094 Tokyo Japan Retrieved from the Internet: URL:http://physics.nist.gov/Divisions/Div844/facilities/photo/Publications/OhnoCIE2004.pdf> [retrieved on apr. 17, 2008] (in English).

* cited by examiner

*Primary Examiner* — Thomas Sember
(74) *Attorney, Agent, or Firm* — Harness, Dickey & Pierce, P.L.C.

(57) ABSTRACT

The present invention relates to an illumination device, comprising a white LED, a red LED and a color filter. A hight color rendering index (CRI, Ra) and a high value of R9 (for strong red) can be obtained. One application is medical lighting, for example for surgical lights.

42 Claims, 9 Drawing Sheets

ILLUMINATION DEVICE

The present invention relates to an illumination device.

In many applications, the spectral characteristics of a lighting system are critical and may be required to meet certain specifications. One particular example of such an application is medical lighting. A large number of devices exist for medical lighting ranging from large aperture operating theatre lights to lights for general examination and simple tasks. The specifications of these devices are the subject of International standard IEC 60601-2-41:2000. The precise characteristics of medical lighting devices are important to a user such as a surgeon, doctor or nurse.

Until recently, the characteristics required of medical lighting devices have been provided using light configurations based on for example tungsten halogen bulbs. These bulbs are usually used in combination with reflector elements to gather the light from the source and project it into a spot or well defined beam 0.5 m-1 m in front of the reflector aperture. In addition, by using heat filter elements in front of the reflector aperture and/or incorporated into the reflector coating, the majority of the infra-red component of the beam can be removed. Colour shift filters are also used to produce specific colour temperatures. For example, Schott Glass type KG1 can be used to shift a tungsten halogen source at a colour temperature of about 3200K up to a colour temperature of ~4300K.

More recently, a number of manufacturers have started to produce medical lighting devices using high brightness light emitting diodes (LEDs). Commercial examples of these include the iled® (Trumpf) which uses white, green and blue LEDs and the PENTALED® (Rimsa) which uses a small number of high power, high lumen output cold white LEDs. Other commercial devices use LEDs to mix in warm white but the lumen output is low. Typically however these devices require a large number of LEDs to produce the requisite light output for medical lighting (eg typically 150 LEDs but often up to 300 LEDs for an operating theatre light). Moreover it is difficult to achieve a good colour rendering index (Ra and R9 in particular are usually low) because of the non-uniform spectral output (ie the spectrum has wavelength gaps). As a result of the large number of LEDs and associated hardware, the devices tend to be expensive with poor optical design and inefficient use of the LED light.

U.S. Pat. No. 6,636,003 discloses an LED arrangement which produces white light with an adjustable colour temperature. The arrangement includes one or more white LEDs and one or more coloured LEDs (eg amber or red and yellow) to produce an output with a desired colour temperature in the range 2500-5000K. The desired colour temperature is adjusted using first and second driver circuits to control the output of the white LEDs and coloured LEDs respectively.

WO-A-01/36864 discloses systems and methods for generating and modulating illumination conditions provided by lighting fixtures with a plurality of LEDs.

The present invention is based on the recognition of a surprising improvement in the spectral characteristics (eg specific colour performance characteristics) of the output light of one or more white LEDs using one or more red LEDs and an optical filter. In particular, the present invention provides an illumination device which transmits light from one or more white LEDs and light from one or more red LEDs through a colour filter to achieve an output with a desirable colour rendering index and colour temperature.

Thus viewed from a first aspect the present invention provides an illumination device capable of emitting an output light comprising:

a housing;
one or more white LEDs emitting a first light along a first path and one or more red LEDs emitting a second light along a second path, wherein the one or more white LEDs and the one or more red LEDs are mounted in the housing such that the first light and the second light are mixed to form the output light transmitted along a third path or to form the output light at a field position; and
a colour filter positioned in one or more of the first path, the second path and the third path.

The illumination device of the present invention advantageously may exhibit a high colour rendering index (as defined in CIE13.3:1995) and/or a useful specific colour temperature. The level of performance is significantly higher than that which can be achieved by using white light LEDs alone or combining white light LEDs with one or more single colour (eg red) LEDs. For example, using a minimal number of high brightness LEDs, an extremely high level of colour performance may be achieved (eg high Ra and R9 can be achieved at a well-defined specific colour temperatures such as 4300K).

Each of the one or more white LEDs and each of the one or more red LEDs may be based on a light emitting polymer, semiconductor dye, organic species, electroluminescent or superluminescent. Specific examples include indium gallium nitride and aluminium indium gallium phosphide.

Each of the one or more white LEDs and each of the one or more red LEDs may be individually mounted in the housing. Each of the one or more white LEDs and each of the one or more red LEDs may be tiltedly mounted in the housing. The output light may take the form of a beam. The output light may be focussed to a spot. By varying the position and tilt of the mounting of the one or more white LEDs or the one or more red LEDs, it is possible in association with beam shaping elements (such as a focussing lens) to achieve a desired beam or spot size, profile and position.

The one or more white LEDs and one or more red LEDs may be clustered. Each cluster may contain only white LEDs or only red LEDs. Each cluster may contain red LEDs and white LEDs which may be randomly distributed. Each cluster may contain red LEDs and white LEDs which may be alternating. In the (or each) cluster, one or more white LEDs may surround a red LED. The cluster may be a regular pattern. The cluster may be a linear, staggered (eg herringbone or honeycomb), triangular, hexagonal or circular pattern.

The one or more white LEDs and one or more red LEDs may be provided in an array. Preferably the array is a plurality of discrete clusters (as described above). The array may be a regular pattern. The array may be a linear, staggered (eg herringbone or honeycomb), triangular, hexagonal or circular pattern.

In a preferred embodiment, the device is a single colour device (ie contains only one colour being the one or more red LEDs).

In a preferred embodiment, each of the one or more white LEDs is a high brightness white LED. Typically the lumen output per Watt is in excess of 15.

In a preferred embodiment, each of the one or more white LEDs is a high power white LED. Typically the input power is 1 W or more.

The one or more white LEDs may be a single white LED. The one or more white LEDs may be 2 or more, preferably 3 or more, particularly preferably 4 or more, especially preferably 5 or more white LEDs.

Each of the white LEDs may be a warm white, neutral white or cold white LED. Preferably each of the one or more white LEDs is a cold white LED. Cold white LEDs suitable for use in this embodiment are available commercially from Lumileds, Edixeon, Nichia, Cree and Osram.

The white LEDs used in accordance with the invention typically have a correlated colour temperature of 4500K or more, preferably in the range 4500 to 10000K, particularly preferably 4500 to 8000K, more preferably 4700 to 7500K, most preferably 5600-7000K.

In a preferred embodiment, the chromaticity coordinate (X) of each of the one or more white LEDs is in the range 0.270 to 0.480, preferably 0.290 to 0.370, particularly preferably 0.300 to 0.330.

In a preferred embodiment, the chromaticity coordinate (Y) of each of the one or more white LEDs is in the range 0.270 to 0.460, preferably 0.270 to 0.400, particularly preferably 0.310 to 0.360.

Preferably each of the one or more white LEDs is selected from a class of LEDs known as LUXEON® (Lumileds). Each LUXEON® white LED may be one from bin NO, NI, PO, PI, QO, RO, RI, RA, UO, UN, UM, VP, VO. VN, VM, WQ, WP, WO, WN, WM, XP, XO, XN, XM, YO or YA. Preferably each LUXEON® white LED is one from bin UO, UN, UM, VP, VO. VN, VM, WQ, WP, WO, WN, WM, XP, XO, XN, XM, YO or YA. Particularly preferred is a LUXEON® white LED from bin XN, XO and WN, more preferably bin XN.

Preferably each of the one or more white LEDs is a LUXEON®, LUXEON® K2, LUXEON® REBEL, LUXEON®III or LUXEON® V LED. An example of a preferred white LED is LUXEON® LXK2-PW14-U00.

The one or more red LEDs may be a single red LED. The one or more red LEDs may be 2 or more, preferably 3 or more, particularly preferably 4 or more, especially preferably 5 or more red LEDs.

The red LED may be a red, red/orange or red/amber LED. Preferably each of the one or more red LEDs has a dominant wavelength in the range 613 to 645 nm, particularly preferably 620 to 631 nm (eg about 627 nm).

Preferably each of the one or more red LEDs is selected from a class of LEDs known as LUXEON® (Lumileds). Particularly preferably the LUXEON® red LED is one from bin 2, 4 or 5.

Preferably each of the one or more red LEDs is a LUXEON®, LUXEON® K2, LUXEON® III, LUXEON® REBEL, LUXEON® Dental or LUXEON® V red LED. Preferred is a LUXEON® K2 red LED. An example of a preferred red LED is LUXEON® LXK2-PD12-R00.

Preferably the illumination device further comprises: one or more converging elements positioned relative to the one or more white LEDs and one or more red LEDs to manipulate the first light and second light to form the output light.

The (or each) converging element may be a focussing element or beam shaping element or beam converging element.

The output light may be converged to a beam or spot. The spot (or beam) size may be 100-400 mm in diameter. The output light may be focussed to a spot (eg a round spot) 0.5 m or more (eg up to 1 m) in front of the device (reference to D10). An advantage of the present invention is that it permits the converging element to produce a broad spot of uniform intensity (in contrast to the Gaussian distribution of the intensity of a spot observed in accordance with conventional arrangements).

The (or each) converging element is preferably a reflector element. The (or each) reflector element may be a beam shaping reflector such as an ellipsoidal reflector element. The LED is typically positioned at or near to a first focal point of the ellipsoidal reflector element.

The spot may be at the second focal point of the ellipsoidal reflector element. The reflector element may be a large aperture reflector element.

In a preferred embodiment, the reflector element is a single reflector element.

In a preferred embodiment, the one or more white LEDs and one or more red LEDs are clustered into a plurality of clusters, wherein the device further comprises:
 a plurality of reflector elements, wherein a reflector element is positioned discretely relative to each cluster to converge the first light and the second light from each cluster to form the output light.

The (or each) converging element is preferably a lens. The lens may be a movable focussing lens. The lens may be a static converging lens. The lens may be a beam shaping lens such as a TIR lens, a spheric or aspheric lens (such as condenser, Fresnel or diffractive lenses). The lens may be a beam converging lens such a wedge lens, Fresnel lens, spheric or aspheric lens.

Preferably the beam size of the first light from the one or more white LEDs is variable relative to the beam size of the second light from the one or more red LEDs. The one or more white LEDs and one or more red LEDs may be clustered and the beam size of the first, second or output light from the clusters may be varied.

In a preferred embodiment, the beam size of the first light from the one or more white LEDs is independently adjustable.

In a preferred embodiment, the beam size of the second light from the one or more red LEDs is independently adjustable.

Preferably the intensity of the first light from the one or more white LEDs is variable relative to the intensity of the second light from the one or more red LEDs. This allows the colour temperature and rendition to be varied.

In a preferred embodiment, the intensity of the first light from each of the one or more white LEDs is independently adjustable.

In a preferred embodiment, the intensity of the second light from the one or more red LEDs is independently adjustable.

In a preferred embodiment, the device is capable of performing solid state focussing.

In a preferred embodiment, the one or more white LEDs and one or more red LEDs are provided in an array, wherein the array is a plurality of discrete first and second clusters. Preferably each first cluster in this embodiment is a cluster of narrow beam LEDs and each second cluster is a cluster of broad beam LEDs. Preferably the beam size of the output light from the first cluster is narrower than the beam size of the output light from the second cluster. The difference between the beam size of the output light from the first cluster and the beam size of the output light from the second cluster may be variable. Alternatively preferably each first cluster and each second cluster in this embodiment is a cluster of narrow beam LEDs and broad beam LEDs. Preferably the intensity of the output light from the first cluster is variable relative to the intensity of the output light from the second cluster. The variability of the intensity permits the beam size (spot diameter) to be controlled (ie change focus) where the narrow and broad beam sizes are fixed.

The device may further comprise a heat sink. Typically the heat sink is mounted rearwardly in the housing. A controller and processor may be included in the device to control the LEDs in accordance with known techniques.

Typically the housing is a luminaire.

In a preferred embodiment, the colour rendering index of the output light is substantially uniform across substantially the whole visible spectrum and is greater than 90.

In a preferred embodiment, the colour rendering index Ra of the output light is 80 or more, preferably 85 or more, particularly preferably 90 or more, more preferably 91 or more, especially preferably 92 or more, most preferably 93 or more.

In a preferred embodiment, the colour rendering index R9 of the output light is 80 or more, preferably 85 or more, particularly preferably 90 or more, more preferably 91 or more, especially preferably 92 or more, most preferably 93 or more.

In a preferred embodiment, each of the colour rendering indices R1 to R8 of the output light is 80 or more, preferably 85 or more, particularly preferably 90 or more, more preferably 91 or more, especially preferably 92 or more, most preferably 93 or more.

In a preferred embodiment, each of the colour rendering indices R1 to R16 of the output light is 80 or more, preferably 85 or more, particularly preferably 90 or more, more preferably 91 or more, especially preferably 92 or more, most preferably 93 or more.

In a preferred embodiment, the output light has a correlated colour temperature in the range 3000 to 6700K, preferably 3000-4500K, particularly preferably 3500 to 4600K, more preferably 4200 to 4400K, yet more preferably about 4300K.

Preferably the colour filter is positioned in the first and/or second path.

Preferably the colour filter is positioned in the first path.

Preferably the colour filter is positioned in the first and second path.

In a preferred embodiment, the colour filter is positioned in the third path.

The colour filter may be composed of a film or sheet (for example a plastic, glass or ceramic film, window or sheet). The colour filter may be mounted in front of, behind or on a surface (eg the rear or front surface) of a converging element such as a converging lens. The colour filter may be transparent, translucent, semi-transparent or semi-translucent. The colour filter may be a dye or laminate on an optical element (eg on a beam shaping element). The colour filter may be a multi-layer interference filter or an absorptive type filter. The colour filter may be a dichroic filter (eg a glass or plastic coated dichroic).

A preferred colour filter is a colour shift filter. Particularly preferred are colour shift filters capable of shifting daylight to tungsten light optionally with a yellow bias.

A preferred colour filter is an amber colour shift filter.
A preferred colour filter is a straw colour shift filter.
A preferred colour filter is a brown colour shift filter.
A preferred colour filter is a yellow colour shift filter.
A preferred colour filter is an orange colour shift filter.
A preferred colour filter is a wheat colour shift filter.

In a preferred embodiment, the chromaticity coordinate (x) of the colour filter is in the range 0.300 to 0.530, preferably 0.320 to 0.460, particularly preferably 0.330 to 0.445, more preferably 0.335 to 0.360.

In a preferred embodiment, the chromaticity coordinate (y) of the colour filter is in the range 0.300 to 0.530, preferably 0.320 to 0.400, particularly preferably 0.335 to 0.395, more preferably 0.340 to 0.360.

In a preferred embodiment, the absorption of the colour filter is 1.0 or less, preferably 0.90 or less, particularly preferably in the range 0.01 to 0.25.

In a preferred embodiment, the transmission (Y %) of the colour filter is in excess of 10, preferably in excess of 15, particularly preferably in the range 70 to 90.

By way of a specific example, a preferred filter is a Lee Lighting 443 Quarter C.T. Straw filter which is capable of shifting light at 6500K to 5100K (daylight to tungsten light with a yellow bias). Other specifically preferred examples include Lee Lighting Filters 206 (which is capable of shifting daylight to tungsten light), 763 (which adds sunlight), 103 (which gives a warm winter effect) and 208 (which is capable of shifting light at 6500K to 3200K (daylight to tungsten light)).

A characteristic of LEDs is that they exhibit a drop in the intensity of output light with a rise in operating temperature. Such a drop can be as much as 10-50% of the initial intensity. An advantage of the present invention is that it permits the drop in intensity to be compensated for.

Thus in a preferred embodiment, the intensity of the output light is substantially constant.

For example, the present invention permits maximum intensity at start-up without using full power. A gradual increase in power from start-up can be exploited to compensate for the drop in intensity.

In a preferred embodiment, the illumination device further comprises:
a measuring device for measuring the operating temperature;
a power device for supplying power to the one or more white LEDs and one or more red LEDs; and
a power adjustment device operatively connected to the measuring device and to the power device, wherein in use the power adjustment device causes the power device to adjust the power supply in response to a change in the operating temperature.

The measuring device may be a thermistor. The power adjustment device may be an integrated circuit.

The device of the present invention may be used in domestic or commercial applications. The applications may be medical (eg surgical or diagnostic) or non-medical (eg in forensic science, retail displays, museums and exhibitions, studio lighting, architectural or machine vision). The device of the present invention may be used in colour matching (eg checking print quality). The device may be chip-mounted. With regard to medical lighting, the device of the invention enables high quality light to be produced from LED sources with excellent colour rendering characteristics at specific colour temperatures. It also enables the colour temperature to be adjusted, by altering the red mix or changing the filter.

From a further patentable viewpoint, the present invention is based on the recognition that an improvement in the spectral characteristics (eg specific colour performance characteristics such as a desirable colour rendering index and colour temperature) of the output light of an illumination device is possible using a specific combination of one or more white LEDs and one or more red LEDs.

Viewed from a further aspect the present invention provides an illumination assembly capable of emitting an output light comprising:
a housing; and
one or more white LEDs emitting a first light along a first path and one or more red LEDs emitting a second light along a second path, wherein the one or more white LEDs and the one or more red LEDs are mounted in the housing such that the first light and the second light are mixed to form the output light transmitted along a third path or to form the output light at a field position, wherein the illumination assembly exhibits a high colour rendering index.

In accordance with the assembly of the invention, using a minimal number of high brightness LEDs, an extremely high level of colour performance may be achieved (eg high Ra and R9 can be achieved at a well-defined specific colour temperatures such as 5600K).

Each of the one or more red LEDs and one or more white LEDs may be as hereinbefore defined. A preferred white LED is a LUXEON® Lumiled selected from the group consisting of bin WN, WO, WX, XN, XO, YA and YO.

In a preferred embodiment of the assembly of the invention, the colour rendering index of the output light is substantially uniform across substantially the whole visible spectrum and is greater than 90.

In a preferred embodiment of the assembly of the invention, the colour rendering index Ra of the output light is 80 or more, preferably 85 or more, particularly preferably 90 or more, more preferably 91 or more, especially preferably 92 or more, most preferably 93 or more (eg about 95).

In a preferred embodiment of the assembly of the invention, the colour rendering index R9 of the output light is 80 or more, preferably 85 or more, particularly preferably 90 or more, more preferably 91 or more, especially preferably 92 or more, most preferably 93 or more.

In a preferred embodiment of the assembly of the invention, each of the colour rendering indices R1 to R8 of the output light is 80 or more, preferably 85 or more, particularly preferably 90 or more, more preferably 91 or more, especially preferably 92 or more, most preferably 93 or more.

In a preferred embodiment of the assembly of the invention, each of the colour rendering indices R1 to R16 of the output light is 80 or more, preferably 85 or more, particularly preferably 90 or more, more preferably 91 or more, especially preferably 92 or more, most preferably 93 or more.

In a preferred embodiment, the output light has a correlated colour temperature in the range 3000 to 6700K, preferably 4500 to 6700K, preferably 4800-6000K, particularly preferably 5000 to 5800K, more preferably about 5600K.

Viewed from a yet further aspect the present invention provides an illumination apparatus capable of emitting an output light comprising:
a housing; and
one or more white LEDs emitting a first light along a first path and one or more red LEDs emitting a second light along a second path, wherein the one or more white LEDs and the one or more red LEDs are mounted in the housing such that the first light and the second light are mixed to form the output light transmitted along a third path or to form the output light at a field position, wherein the one or more white LEDs and one or more red LEDs are clustered into a plurality of clusters and the beam size of the first, second or output light from the clusters is variable.

The apparatus may further comprise:
a plurality of converging elements, wherein a converging element is positioned discretely relative to each cluster to converge the first light and the second light from each cluster to form the output light. Each converging element may be as hereinbefore defined.

In a preferred embodiment of the apparatus of the invention, the beam size of the first light from the one or more white LEDs is independently adjustable.

In a preferred embodiment of the apparatus of the invention, the beam size of the second light from the one or more red LEDs is independently adjustable.

Preferably the intensity of the first light from the one or more white LEDs is variable relative to the intensity of the second light from the one or more red LEDs.

In a preferred embodiment of the apparatus of the invention, the intensity of the first light from each of the one or more white LEDs is independently adjustable.

In a preferred embodiment of the apparatus of the invention, the intensity of the second light from the one or more red LEDs is independently adjustable.

In a preferred embodiment of the apparatus of the invention, the device is capable of performing solid state focussing.

In a preferred embodiment of the apparatus of the invention, the one or more white LEDs and one or more red LEDs are provided in an array, wherein the array is a plurality of discrete first and second clusters. Preferably each first cluster in this embodiment is a cluster of narrow beam LEDs and each second cluster is a cluster of broad beam LEDs. Preferably the beam size of the output light from the first cluster is narrower than the beam size of the output light from the second cluster. The difference between the beam size of the output light from the first cluster and the beam size of the output light from the second cluster may be variable. Alternatively preferably each first cluster and each second cluster in this embodiment is a cluster of narrow beam LEDs and broad beam LEDs. Preferably the intensity of the output light from the first cluster is variable relative to the intensity of the output light from the second cluster. The variability of the intensity permits the beam size (spot diameter) to be controlled (ie change focus) where the narrow and broad beam sizes are fixed.

The present invention will now be described in a non-limitative sense with reference to examples and to the accompanying Figures in which.

Figure 4:
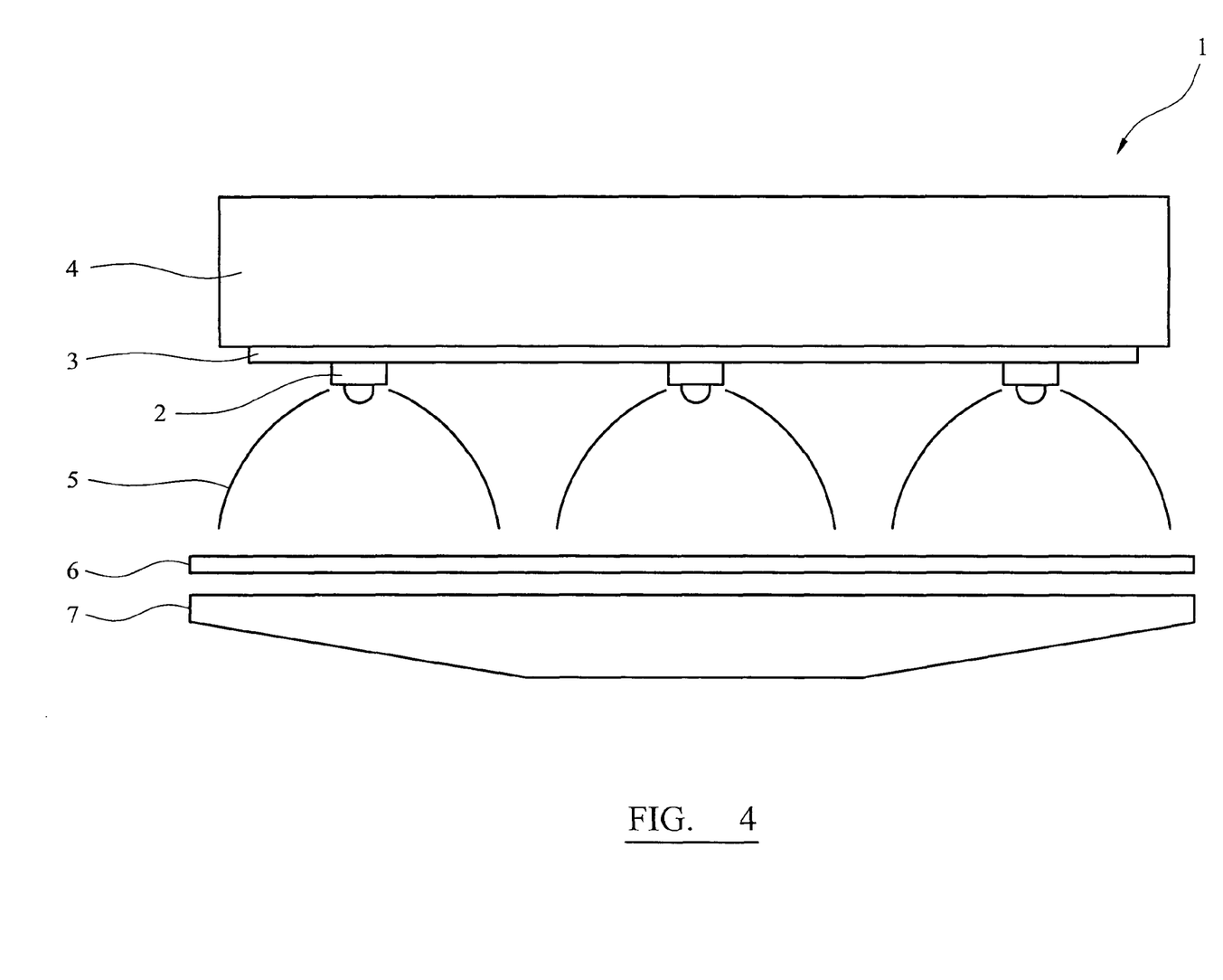
FIG. 4: A first embodiment of the illumination device of the invention shown schematically in cross-section.

A first embodiment of the illumination device of the invention 1 is illustrated schematically in cross-section in FIG. 4. One or more white LEDs and one or more red LEDs 2 on a printed circuit board 3 are mounted in a housing (not shown). To the rear of the printed circuit board 3 is a heatsink 4. Each LED 2 is equipped with a beam shaping reflector 5. Light from the white and red LEDs passes through a colour filter 6 and a wedge lens 7 which converges and mixes the light beam transmitted through the filter into an output light to a spot.

Figures 5A, 5B, 5C:
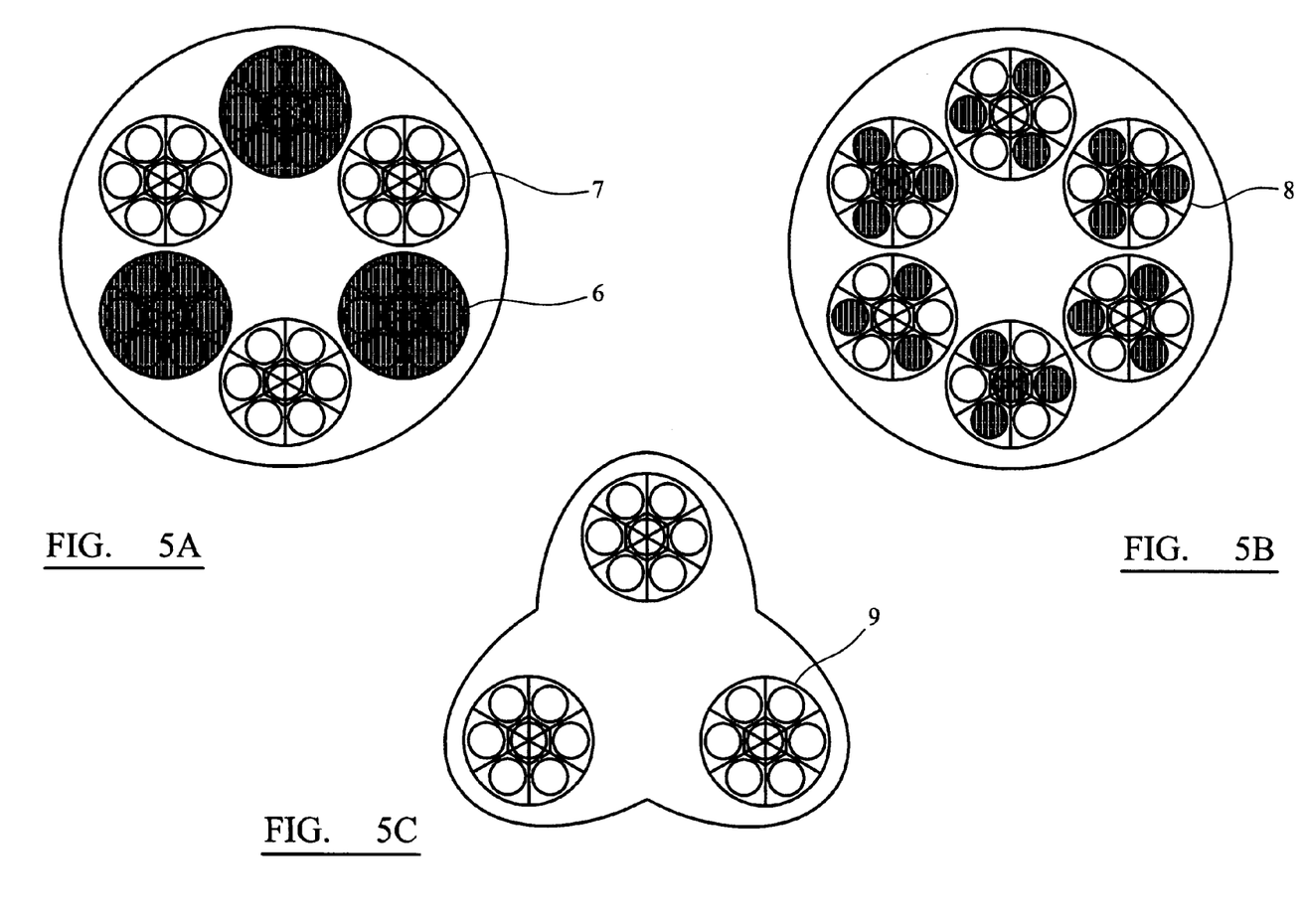
FIGS. 5A to 5D: A plan view of a second, third, fourth and fifth embodiment of the invention.

FIGS. 5A to 5C illustrate in plan view second, third and fourth embodiments of the illumination device of the invention with a similar arrangement of parts to that of FIG. 4 described above. In these embodiments, narrow beam and wide beam white LEDs and red LEDs are disposed in an array of hexagonal clusters. In each hexagonal cluster, a red LED sits at the centre of the white LEDs.

In the second embodiment (FIG. 5A), hexagonal clusters 6 of narrow beam red LEDs and white LEDs (shaded) and hexagonal clusters 7 of wide beam white LEDs and red LEDs (unshaded) are disposed in a hexagonal array which is capable of solid state focussing (and which constitutes an embodiment of the apparatus of the invention). A red LED lies at the centre of the array.

In the third embodiment (FIG. 5B), hexagonal clusters 8 of alternating narrow beam (shaded) and wide beam (unshaded) white and red LEDs are in a hexagonal array which is capable of solid state focussing (and which constitutes an embodiment of the apparatus of the invention). A red LED lies at the centre of the array.

In the fourth embodiment (FIG. 5C), hexagonal clusters 9 of narrow beam (unshaded) white and red LEDs are in a triangular array which is incapable of solid state focussing. A red LED lies at the centre of the array.

Figure 5D:
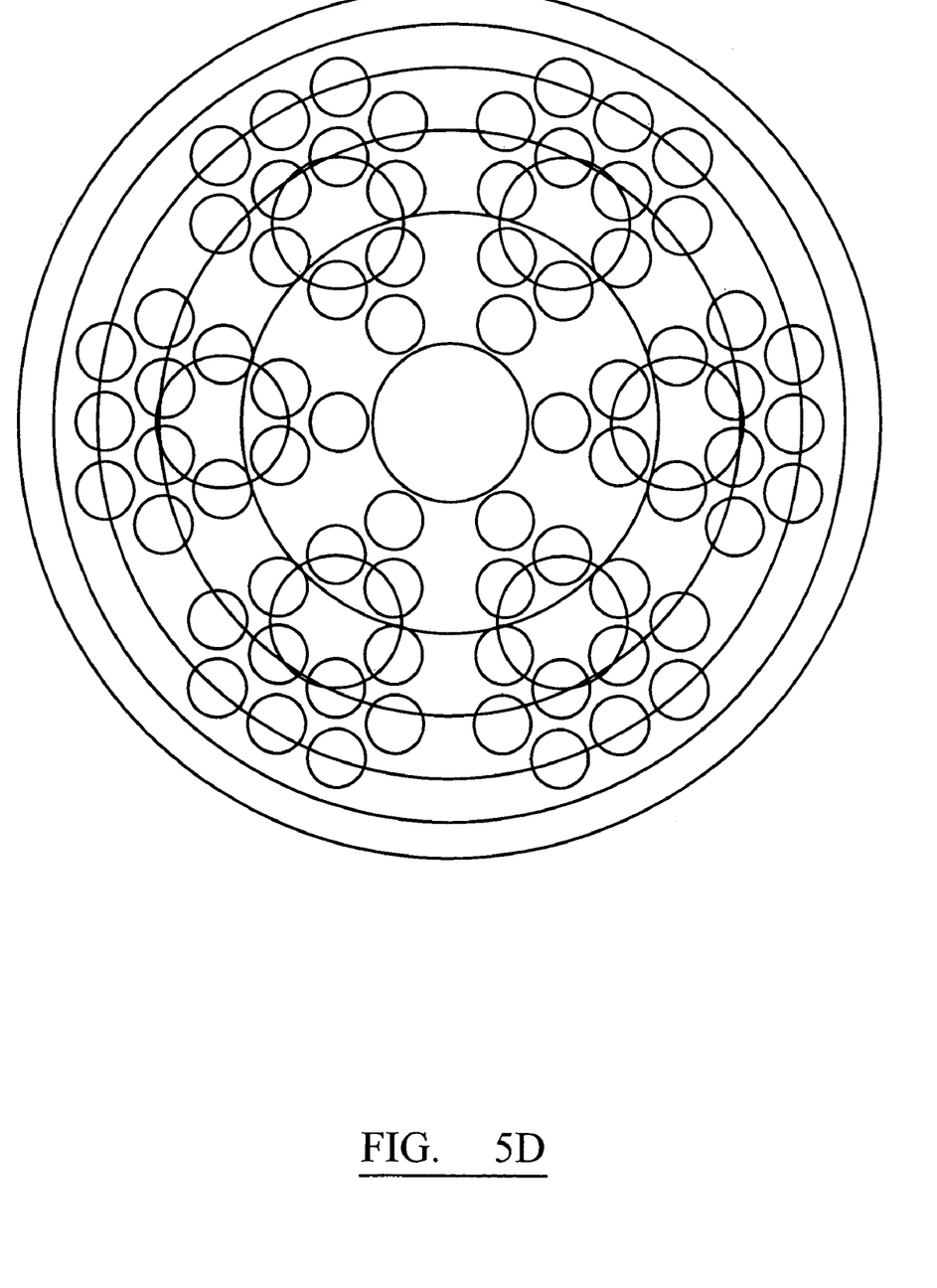

FIG. 5D illustrates in plan view a fifth embodiment with a similar arrangement of parts to that of FIG. 4 described above or FIG. 6 described below. In this embodiment, white LEDs and red LEDs are disposed in a complex array.

Figure 6:
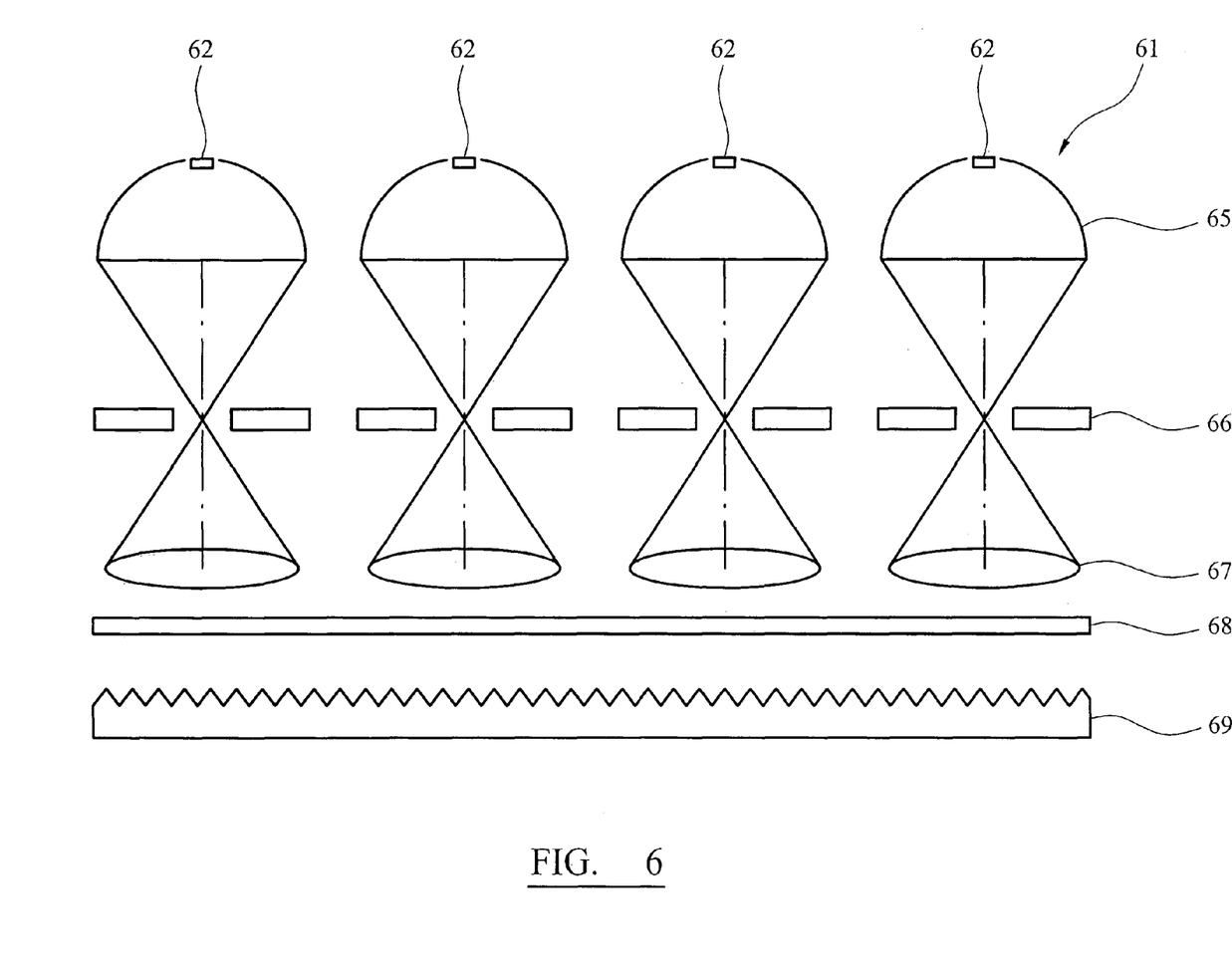
FIG. 6: A sixth embodiment of the illumination device of the invention shown schematically in cross-section.

A sixth embodiment of the device of the invention 61 is illustrated schematically in cross-section in FIG. 6. One or more white LEDs and one or more red LEDs 62 are mounted in a housing (not shown). Each LED 62 is positioned at a first focal point of an ellipsoidal reflector 65 which re-images the LED to the second focus of the ellipsoidal reflector 65 which is approximately in the same plane as an array of apertures 66. This second focus is then re-imaged by an array of lenses 67 to the field of interest (0.5-1 m away). Mixed light from the white and red LEDs 62 passes through a colour filter 68 and a converging Fresnel lens 69 which converges the light transmitted through the filter 68 into an output light beam focussed onto a spot. By mechanically moving the array of lenses 67 the spot size at the field position can be adjusted. This gives a mechanical means for adjusting the beam size.

Figure 7:
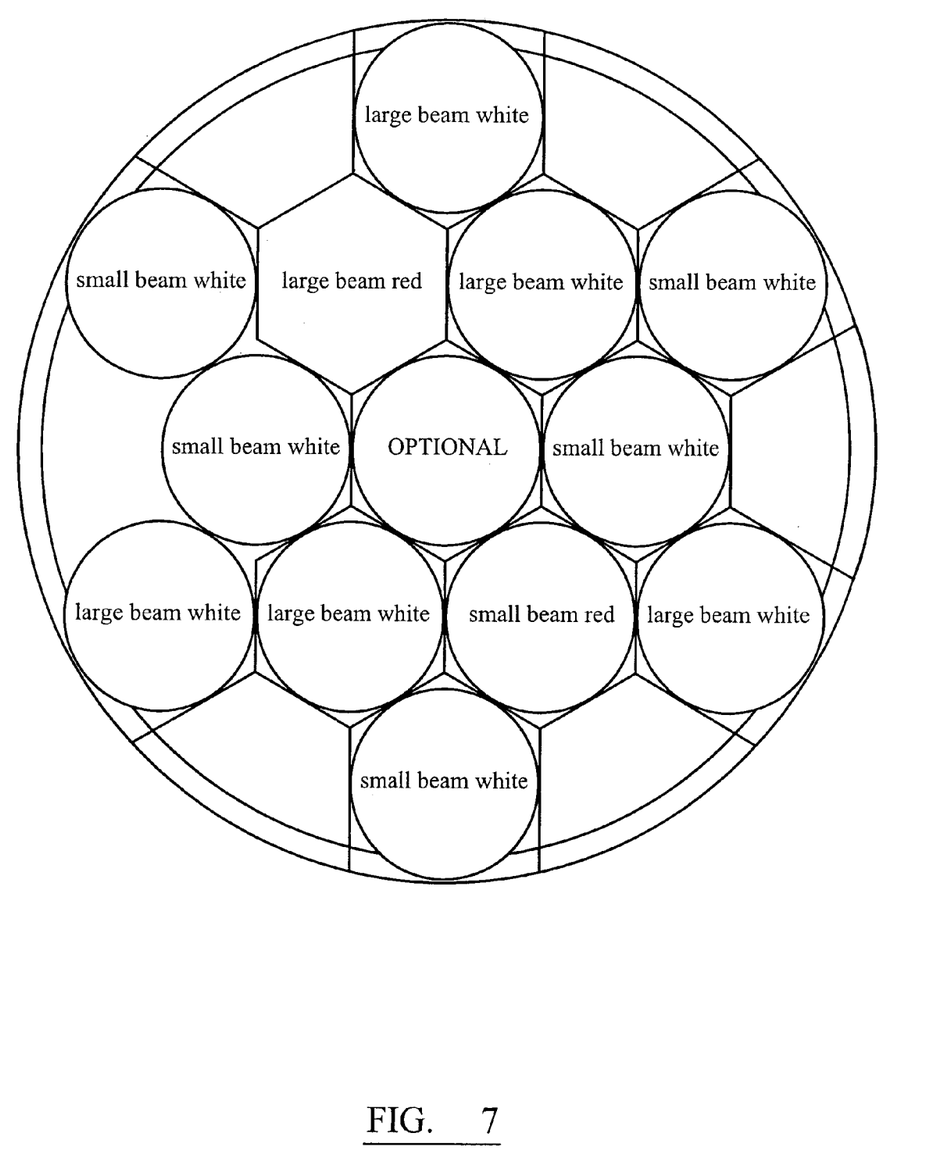
FIG. 7: A plan view of a seventh embodiment of the illumination device of the invention.

FIG. 7 illustrates in plan view a seventh embodiment with a similar arrangement of parts to that of FIGS. 4 and 5 described above. White LEDs and red LEDs are disposed in a honeycomb array with varying beam sizes (as denoted) to permit solid state focussing (and which therefore constitutes an embodiment of the apparatus of the invention).

Figure 8:
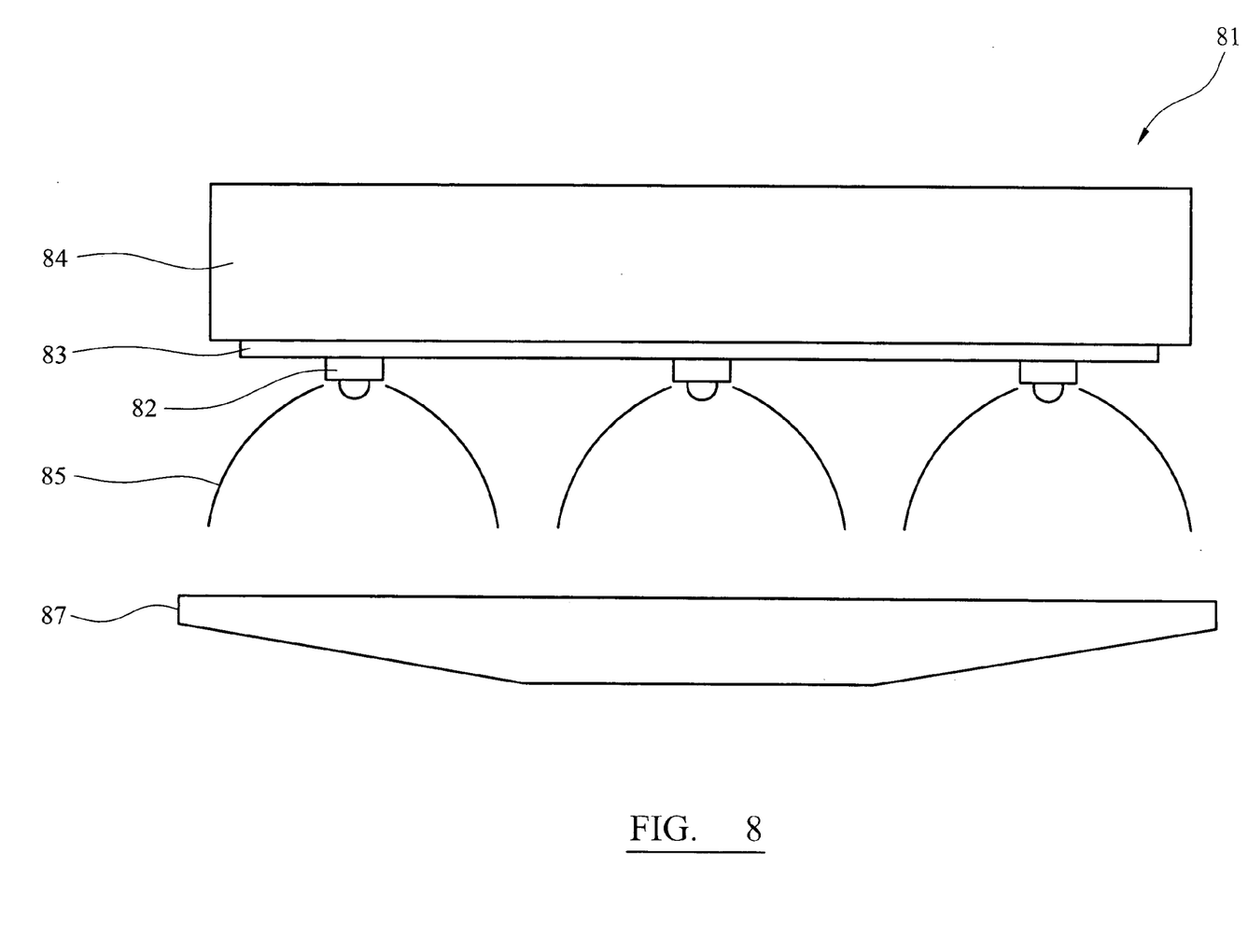
FIG. 8: A first embodiment of the illumination assembly of the invention shown schematically in cross-section.

A first embodiment of the illumination assembly of the invention 81 is illustrated schematically in cross-section in FIG. 8. One or more white LEDs and one or more red LEDs 82 on a printed circuit board 83 are mounted in a housing (not shown). To the rear of the printed circuit board 83 is a heatsink 84. Each LED 82 is equipped with a beam shaping reflector 85. Light from the white and red LEDs passes through a wedge lens 87 which converges and mixes the light beam into an output light to a spot.

Figure 9:
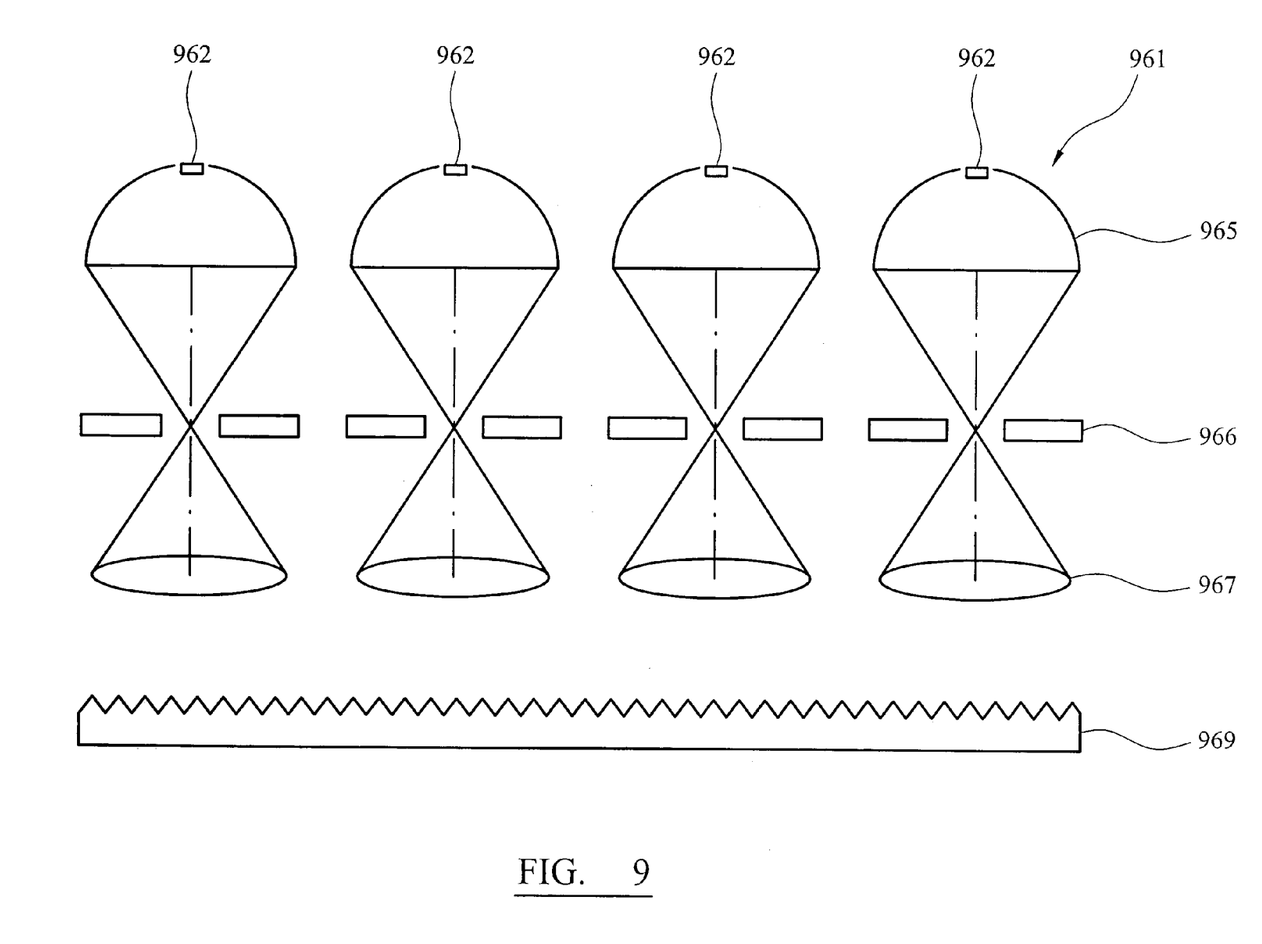
FIG. 9: A second embodiment of the illumination assembly of the invention shown schematically in cross-section.

A second embodiment of the illumination assembly of the invention 961 is illustrated schematically in cross-section in FIG. 9. One or more white LEDs and one or more red LEDs 962 are mounted in a housing (not shown). Each LED 962 is positioned at a first focal point of an ellipsoidal reflector 965 which re-images the LED to the second focus of the ellipsoidal reflector 965 which is approximately in the same plane as an array of apertures 966. This second focus is then re-imaged by an array of lenses 967 to the field of interest (0.5-1 m away). Mixed light from the white and red LEDs 962 passes through a converging Fresnel lens 969 which converges the light transmitted through the filter 968 into an output light beam focussed onto a spot. By mechanically moving the array of lenses 967, the spot size at the field position can be adjusted. This gives a mechanical means for adjusting the beam size.

EXAMPLE

Figure 1:
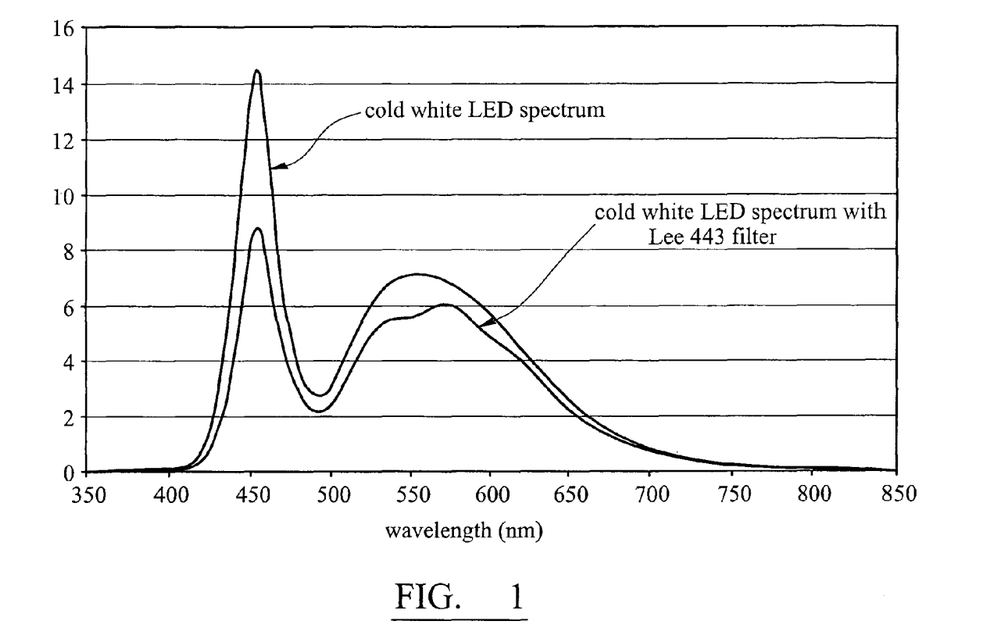
FIG. 1: Cold white LED spectrum before and after applying a Lee 443 colour shift filter.

The upper trace in FIG. 1 shows the spectral characteristics of a cold white LUXEON® K2 LED which has been binned by the manufacturer to ensure that it has a correlated colour temperature in the region of ~7000K (part number 1XK2-PW14-U00). The Ra, R9 and correlated colour temperature of this LED alone is unsuitable for medical lighting purposes. However the high lumens output means that the LED is capable of achieving the high lux levels required for medical applications if used in conjunction with an appropriate optical arrangement (usually a lens or reflector).

By passing the light from this LED through a colour shift filter, the colour temperature can be adjusted. The lower trace in FIG. 1 shows the spectrum of the light after passing through the filter. The primary effect is the attenuation of the main wavelength peak around 450 nm and the slight modification of the shape of the curve around a wavelength of ~520 to ~630 nm. The net effect of this is that the correlated colour temperature is shifted down from ~7000K to ~5500K. In addition, the colour rendition of the source is improved.

Figure 2:
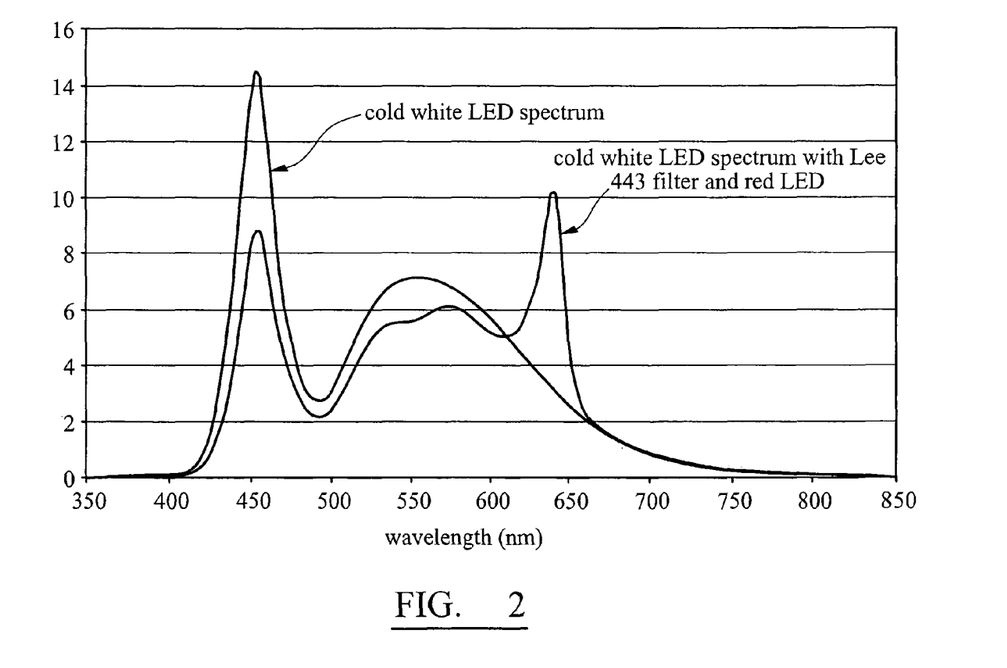
FIG. 2: Cold white LED spectrum shown before and after applying a Lee 443 colour shift filter and additional light from a red LED.

By adding a red LUXEON® K2 red LED (part number LXK2-PD12-R00) which has a typical dominant wavelength of ~627 nm, the spectrum shifts to that shown in FIG. 2. The effect of adding the red light is to further shift the correlated colour temperature down to ~4300K. In addition, colour rendition is further improved. As a result, the light produced by the combination of the white LEDS, the red LED and the filter has almost ideal characteristics for medical lighting ie it has excellent colour rendition at a desirable correlated colour temperature. By varying the amount of red, it is possible to vary the colour temperature. Optimum colour rendition can be achieved for a specific filter at a specific CCT with a specific amount of red light. By changing the amount of red and the filter type, it may be possible to good overall performance at a different cct.

TABLE 1

Measured colour parameters from light generated using a cold white LED, Lee 443 filter and red LED.

| | |
|---|---|
| CRI R1 | 96.4 (4394 K) |
| CRI R2 | 95.9 (4394 K) |
| CRI R3 | 90.1 (4394 K) |
| CRI R4 | 94.4 (4394 K) |
| CRI R5 | 94.1 (4394 K) |
| CRI R6 | 90.8 (4394 K) |
| CRI R7 | 98.2 (4394 K) |
| CRI R8 | 96.9 (4394 K) |
| CRI R9 | 93.4 (4394 K) |
| CRI R10 | 86.0 (4394 K) |
| CRI R11 | 91.4 (4394 K) |
| CRI R12 | 82.8 (4394 K) |
| CRI R13 | 96.1 (4394 K) |
| CRI R14 | 93.5 (4394 K) |

Table 1 shows the measured colour characteristics of the device shown in FIG. 2. Ra (about 95) and R9 are high which is important for medical lighting applications. The measured correlated colour temperature of this source is close to the desirable value of 4300K.

Figure 3:
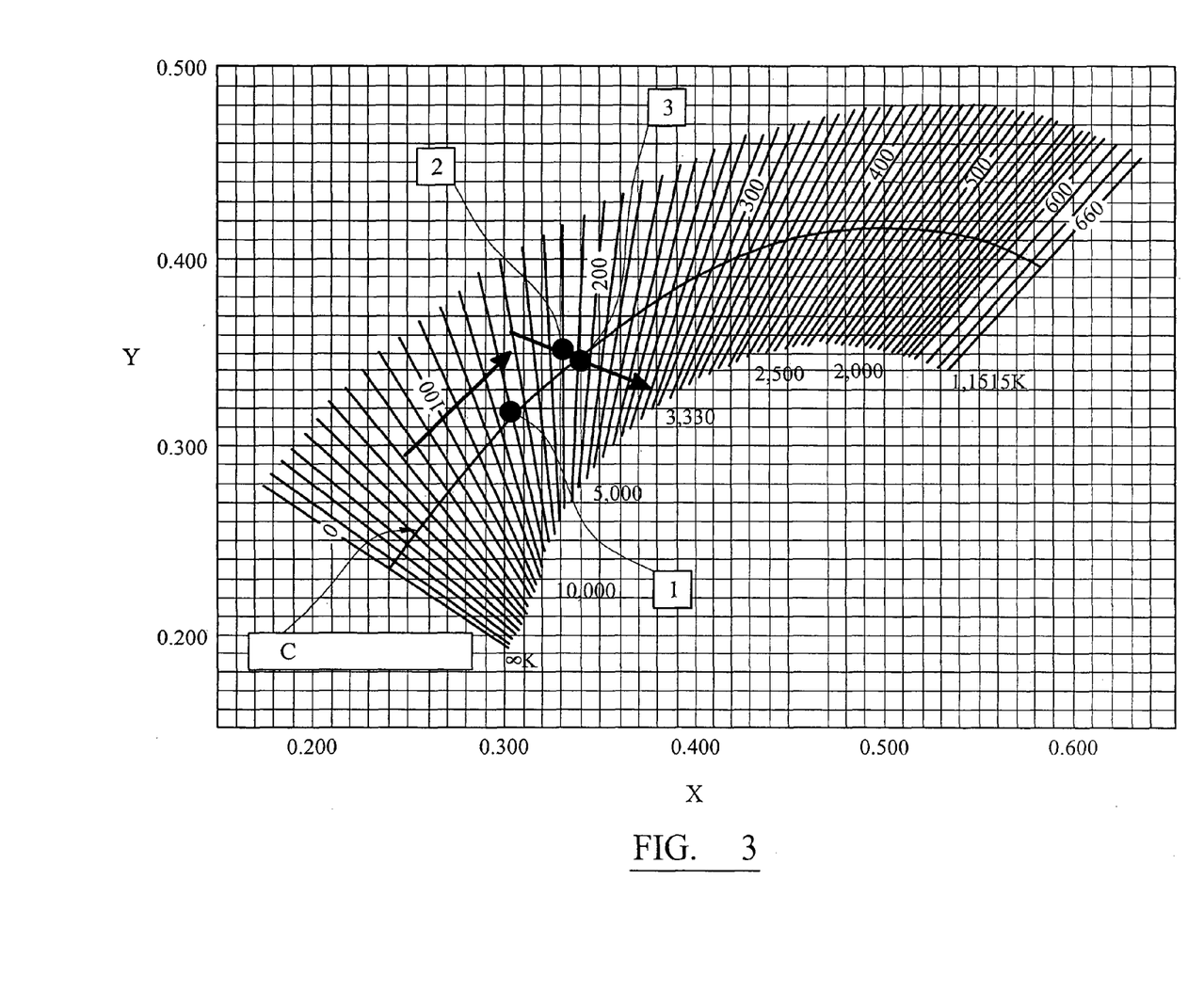
FIG. 3: Chromaticity diagram showing the effect of filtering and mixing LEDs.

FIG. 3 shows a standard chromaticity diagram taken from Wyszecki & Stiles, Colour Science, Second Edition, 2000. The blackbody curve C is represented in the graph along with the lines which show the distribution of colour temperatures. The cold white LED source in this Example sits in position 1 (slightly above the blackbody curve with a correlated colour temperature of ~7000K). The effect of adding the colour filter is to shift the source along the blackbody curve in the direction of the first arrow as shown to position 2. In position 2, the colour temperature remains high. Adding light from a red LED shifts the light in the direction shown by the second arrow towards the red end of the chromaticity diagram (towards the bottom right) to position 3. The light now has a lower colour temperature and sits very close to the blackbody curve. The colour characteristics approximate to those of a blackbody (which has excellent colour rendition).

The invention claimed is:

1. An illumination device capable of emitting an output light comprising:
   a housing;
   one or more white LEDs emitting a first light along a first path and one or more red LEDs emitting a second light along a second path, wherein the one or more white LEDs and the one or more red LEDs are mounted in the housing such that the first light and the second light are mixed to form an output light transmitted along a third path or to form an output light at a field position; and
   a colour filter positioned in one or more of the first path, the second path and the third path,
   wherein a chromaticity coordinate X of each of the one or more white LEDs is in a range 0.270 to 0.480 and a chromaticity coordinate Y of each of the one or more white LEDs is in a range 0.270 to 0.460 and wherein the or each red LED has a dominant wavelength in a range 613 to 645 nm,
   wherein a colour rendering index Ra of the output light is 80 or more.

2. An illumination device as claimed in claim 1 wherein one or more white LEDs and one or more red LEDs are clustered.

3. An illumination device as claimed in claim 1 wherein one or more white LEDs and one or more red LEDs are provided in an array.

4. An illumination device as claimed in claim 3 wherein the array is a plurality of discrete clusters.

5. An illumination device as claimed in claim 4 wherein each cluster is a linear, staggered, herringbone, honeycomb, triangular, hexagonal or circular pattern.

6. An illumination device as claimed in claim 3 wherein each cluster is a linear, staggered, herringbone, honeycomb, triangular, hexagonal or circular pattern.

7. An illumination device as claimed in any preceding claim 1 wherein each white LED is a high brightness white LED.

8. An illumination device as claimed in claim 1 wherein each white LED is a high power white LED.

9. An illumination device as claimed in claim 1 wherein the one or more white LEDs is a plurality of white LEDs.

10. An illumination device as claimed in any preceding claim 1 wherein the or each white LED is a cold white LED.

11. An illumination device as claimed in any claim 1 wherein the or each white LED has a correlated colour temperature of 4500K or more.

12. An illumination device as claimed in claim 1 wherein the or each red LED is a red, red/orange or red/amber LED.

13. An illumination device as claimed in claim 1 wherein the or each red LED has a dominant wavelength in the range 620 to 631 nm.

14. An illumination device as claimed in claim 1 further comprising: one or more converging elements positioned relative to the one or more white LEDs and one or more red LEDs to manipulate the first light and second light to form the output light.

15. An illumination device as claimed in claim 14 wherein the or each converging element is a focussing element, beam shaping element or beam converging element.

16. An illumination device as claimed in claim 1 wherein a beam size of the first, second or output light is variable.

17. An illumination device as claimed in claim 1 wherein an intensity of the first light from the one or more white LEDs is variable relative to an intensity of the second light from the one or more red LEDs.

18. An illumination device as claimed in claim 1 wherein the one or more white LEDs and one or more red LEDs are provided in an array, wherein the array is a plurality of discrete first and second clusters.

19. An illumination device as claimed in claim 1 wherein the colour rendering index of the output light is substantially uniform across substantially a whole visible spectrum and is greater than 90.

20. An illumination device as claimed in claim 1 wherein the colour rendering index Ra of the output light is 85 or more.

21. An illumination device as claimed in claim 1 wherein a colour rendering index R9 of the output light is 80 or more.

22. An illumination device as claimed in claim 1 wherein each of a range of colour rendering indices R1 to R8 of the output light is 80 or more.

23. An illumination device as claimed in claim 1 wherein each of a range of colour rendering indices R1 to R16 of the output light is 80 or more.

24. An illumination device as claimed in claim 1 wherein the output light has a correlated colour temperature in the range 3000 to 6700K.

25. An illumination device as claimed in claim 1 wherein the colour filter is positioned in the first and/or second path.

26. An illumination device as claimed in claim 1 wherein the colour filter is a colour shift filter.

27. An illumination device as claimed in claim 1 wherein the chromaticity coordinate (x) of the colour filter is in the range 0.300 to 0.530.

28. An illumination device as claimed in any preceding claim 1 wherein the chromaticity coordinate (y) of the colour filter is in the range 0.300 to 0.530.

29. An illumination device as claimed in claim 1 wherein the or each white LED has a correlated colour temperature in a range of 5600 to 7000K.

30. An illumination device as claimed in claim 1 wherein the colour rendering index Ra of the output light is 93 or more.

31. An illumination device as claimed in claim 1 wherein a colour rendering index R9 of the output light is 93 or more.

32. An illumination device as claimed in claim 1 wherein each of a range of the colour rendering indices R1 to R8 of the output light is 93 or more.

33. An illumination device as claimed in claim 1 wherein each of a range of the colour rendering indices R1 to R16 of the output light is 93 or more.

34. An illumination device as claimed in claim 1 wherein the output light has a correlated colour temperature of about 4300K.

35. An illumination device as claimed in claim 1 wherein the chromaticity coordinate (x) of the colour filter is in a range 0.335 to 0.360.

36. An illumination device as claimed in claim 1 wherein the chromaticity coordinate (y) of the colour filter is in a range 0.340 to 0.360.

37. An illumination device capable of emitting an output light comprising:
   a housing;
   one or more white LEDs emitting a first light along a first path and one or more red LEDs emitting a second light along a second path, wherein the one or more white LEDs and the one or more red LEDs are mounted in the housing such that the first light and the second light are mixed to form an output light transmitted along a third path or to form an output light at a field position; and
   a colour filter positioned in one or more of the first path, the second path and the third path,
   wherein the one or more white LEDs and one or more red LEDs are provided in an array, wherein the array is a plurality of discrete first and second clusters; and
   wherein each first cluster is a cluster of narrow beam LEDs and each second cluster is a cluster of broad beam LEDs.

38. An illumination device as claimed in claim 37 wherein the beam size of the output light from the first cluster is narrower than the beam size of the output light from the second cluster.

39. An illumination device as claimed in claim 37 wherein an intensity of the output light from the first cluster is variable relative to an intensity of the output light from the second cluster.

40. An illumination device as claimed in claim 38 wherein an intensity of the output light from the first cluster is variable relative to an intensity of the output light from the second cluster.

41. An illumination device capable of emitting an output light comprising:
   a housing;
   one or more white LEDs emitting a first light along a first path and one or more red LEDs emitting a second light along a second path, wherein the one or more white LEDs and the one or more red LEDs are mounted in the housing such that the first light and the second light are mixed to form an output light transmitted along a third path or to form an output light at a field position; and
   a colour filter positioned in one or more of the first path, the second path and the third path,
   wherein the one or more white LEDs and one or more red LEDs are provided in an array, wherein the array is a plurality of discrete first and second clusters; and
   wherein each first cluster and each second cluster is a cluster of narrow beam LEDs and broad beam LEDs.

42. An illumination device as claimed in claim 41 wherein an intensity of the output light from the first cluster is variable relative to an intensity of the output light from the second cluster.

* * * * *

UNITED STATES PATENT AND TRADEMARK OFFICE
CERTIFICATE OF CORRECTION

| | | |
|---|---|---|
| PATENT NO. | : 8,201,966 B2 | Page 1 of 1 |
| APPLICATION NO. | : 12/523426 | |
| DATED | : June 19, 2012 | |
| INVENTOR(S) | : Graeme Hall et al. | |

It is certified that error appears in the above-identified patent and that said Letters Patent is hereby corrected as shown below:

In the Claims:

Column 11, Claim 1, Line 17, "range" should be --range of--

Column 11, Claim 1, Line 18, "range" should be --range of--

Column 11, Claim 1, Line 20, "wherein" should be --whereby--

Column 11, Claim 7, Line 35, delete "any preceding" prior to claim 1

Column 11, Claim 10, Line 42, delete "any preceding" prior to claim 1

Column 11, Claim 11, Line 43, "any claim 1" should be --claim 1--

Column 12, Claim 28, Line 24, delete "any preceding" prior to claim 1

Column 12, Claim 35, Line 43, "in a range" should be --in a range of--

Column 12, Claim 36, Line 46, "in a range" should be --in a range of--

Signed and Sealed this
Ninth Day of October, 2012

David J. Kappos
*Director of the United States Patent and Trademark Office*